United States Patent [19]

White et al.

[11] Patent Number: 5,246,751
[45] Date of Patent: Sep. 21, 1993

[54] POLY(HYDROXY ETHER IMIDES) AS BARRIER PACKAGING MATERIALS

[75] Inventors: Jerry E. White; Edmund J. Stark; Anthony P. Haag; Daniel J. Murray, all of Midland, Mich.

[73] Assignee: The Dow Chemical Company, Midland, Mich.

[21] Appl. No.: 884,673

[22] Filed: May 18, 1992

[51] Int. Cl.$^5$ .................. B29D 22/00; B29D 23/00; C08G 59/00; C08G 65/08

[52] U.S. Cl. .................. 428/35.4; 428/36.6; 428/36.7; 428/412; 428/413; 428/414; 428/480; 428/516; 428/523; 525/523; 525/533; 528/96

[58] Field of Search .............. 528/96; 428/36.6, 36.7, 428/413, 35.4, 412, 414, 480, 516, 523; 525/523, 533

[56] References Cited

U.S. PATENT DOCUMENTS

| | | | |
|---|---|---|---|
| 3,346,665 | 10/1967 | Schwarzer et al. | 525/504 |
| 3,920,768 | 11/1975 | Kwiatkowski | 525/421 |
| 4,052,366 | 10/1977 | Harbermeier et al. | 528/96 |
| 4,163,097 | 7/1979 | Baumann et al. | 525/530 |
| 4,176,223 | 11/1979 | Irwin | 528/170 |
| 4,283,521 | 8/1981 | Jones | 528/117 |
| 4,340,455 | 7/1982 | Kempter et al. | 204/181.7 |
| 4,346,206 | 8/1982 | Takahashi et al. | 528/88 |
| 4,366,302 | 12/1982 | Gounder et al. | 528/99 |
| 4,393,188 | 7/1983 | Takahashi et al. | 528/88 |
| 4,632,972 | 12/1986 | Hefner, Jr. et al. | 528/96 |
| 4,636,542 | 1/1987 | Hefner, Jr. et al. | 523/466 |
| 4,649,187 | 3/1987 | Hefner, Jr. et al. | 528/117 |
| 4,705,833 | 11/1987 | Saito et al. | 525/504 |
| 4,723,916 | 6/1988 | Jones | 528/117 |
| 4,760,105 | 7/1988 | Fuller et al. | 523/420 |
| 4,786,668 | 11/1988 | Dewhirst | 528/104 |
| 4,786,669 | 11/1988 | Dewhirst | 528/97 |
| 4,888,407 | 12/1989 | Yasuhisa et al. | 525/423 |
| 4,960,860 | 10/1990 | Saito et al. | 528/353 |
| 4,985,529 | 1/1991 | Saito et al. | 528/96 |
| 5,075,410 | 12/1991 | Arpin | 528/96 |

FOREIGN PATENT DOCUMENTS

| | | |
|---|---|---|
| 49-38119 | 10/1974 | Japan . |
| 7438119 | 10/1974 | Japan . |
| 54-64597 | 5/1979 | Japan . |
| 1-063952 | 3/1989 | Japan . |
| 0270723 | 3/1990 | Japan . |

OTHER PUBLICATIONS

J. Polym. Sci., Polym. Chem. Ed. 1982, 20(4), 1107–1117 (CA97:92887y).

Pollimo 1982, 6(1), 36–44 (CA92:200297w).

Primary Examiner—Frederick F. Krass

[57] ABSTRACT

Hydroxy-functionalized polyethers having imide groups in their backbones are prepared by contacting an imide-containing bisphenol with the diglycidyl ether of the same or another bisphenol under conditions sufficient to cause the nucleophilic phenolic hydroxyl moieties to react with epoxy groups. These poly(hydroxy ether imides) possess a combination of high barrier to oxygen transmission (i.e., oxygen transmission rates of less than 10.0 cm$^3$-mil/100 in$^2$-atm-day) and high heat resistance (i.e., $T_g$ above 120° C.). These polymers are suitable for use in the manufacture of packaging materials with high barrier to oxygen.

9 Claims, No Drawings

POLY(HYDROXY ETHER IMIDES) AS BARRIER PACKAGING MATERIALS

BACKGROUND OF THE INVENTION

This invention relates to thermoplastic polymers having pendant hydroxyl moieties and phenoxyether moieties and to articles prepared from such polymers.

Hydroxyphenoxyether polymers have good barrier to oxygen, having oxygen transmission rates (OTR) of less than 10 cm$^3$-mil/100 in$^2$-atm-day. These polymers are therefore useful in packaging oxygen-sensitive materials. See, for example, Reinking et al, J. Poly Sci., Vol. 7, pp. 2135-2144, pp. 2145-2152 and pp. 2153-2160 (1963) and Encyclopedia of Polymer Science and Technology, Vol. 10, pp. 111-122. However, these hydroxyphenoxyether polymers have only moderate heat resistance, typified by glass transition temperatures ($T_g$) below about 115° C. Attempts have been made to increase the heat resistance of these hydroxyphenoxyether polymers. However, hydroxyphenoxyether polymers modified to exhibit increased heat resistance and exhibit $T_g$ above 115° C. generally suffer diminished barrier performance with OTR as high as 75 cm$^3$-mil/100 in$^2$-atm-day.

In view of the limited barrier properties and heat resistance of polymers having pendant hydroxyl moieties and phenoxyether moieties, it would be highly desirable to provide a polymer possessing a combination of genuinely good barrier (i.e., oxygen transmission rate less than 10.0 cm$^3$-mil/100in$^2$-atm-day) and high heat resistance (i.e., $T_g$ above 120° C.).

SUMMARY OF THE INVENTION

The present invention is, in one aspect, a polymer having at least one imide group per repeat unit in its backbone and pendant hydroxyl moieties and phenoxyether moieties.

In a second aspect, this invention is a hot-fillable or retort-sterilizable packaging material fabricated of the above hydroxyphenoxy polymer. In yet a further aspect, this invention is a hot-fillable or retort-sterilizable, substantially impermeable film or coating of the polymer.

In addition to their use as barrier containers and films, the polymers of this invention are also useful as molding, extrusion and casting resins.

DETAILED DESCRIPTION OF ILLUSTRATIVE EMBODIMENTS

Preferably, the polymer of this invention has repeating units represented by the formula:

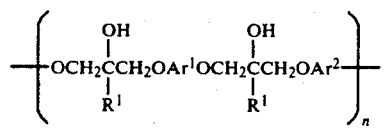

wherein n is an integer from 10 to 1000, R$^1$ is independently a hydrogen or hydrocarbyl moiety, Ar$^1$ is an arylene linkage, and Ar$^2$ is an imide-containing arylene linkage represented by any one of the formulae:

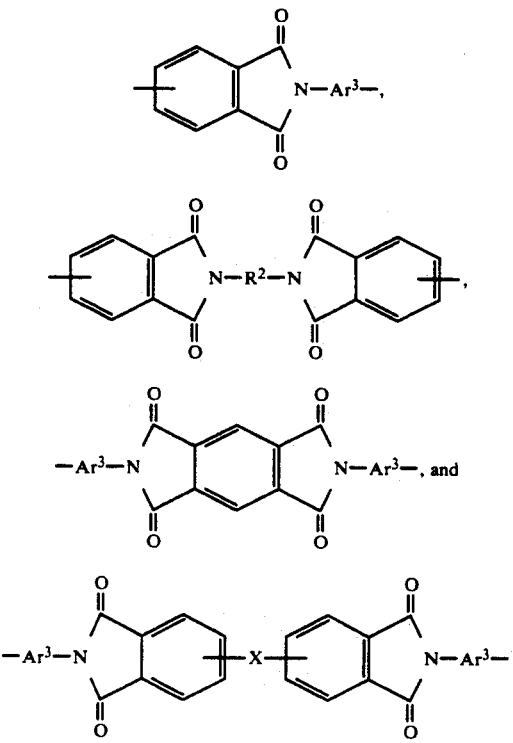

wherein R$^2$ is hydrocarbylene segment that is primarily hydrocarbon but can contain hetero atoms such as sulfur, oxygen or nitrogen, X is a linking group such as a covalent bond, hydrocarbylene, oxygen, sulfur, sulfonyl, or carbonyl, and Ar$^3$ has one of the formulae:

wherein R$^3$ is a hydrogen, hydrocarbyl, substituted hydrocarbyl, wherein the substituent(s) is a monovalent moiety which is inert in the reactions used to prepare the polymer, halo or cyano moiety and Y is defined as a

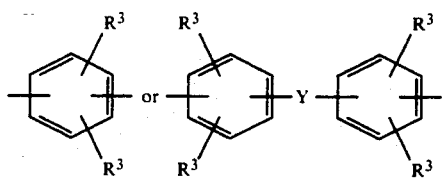

covalent bond, hydrocarbylene, oxygen, sulfur, sulfonyl, carbonyl and the like.

In a more preferred embodiment, R$^1$ is hydrogen, Ar$^1$ is a 4,4'-isopropylidenediphenyl linkage and Ar$^2$ is represented by any one of the formulae:

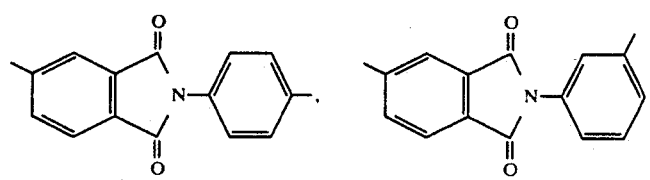

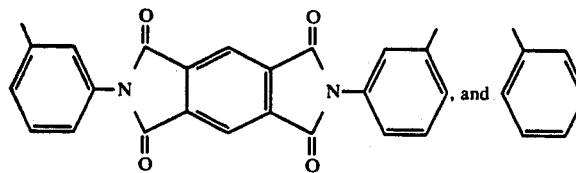 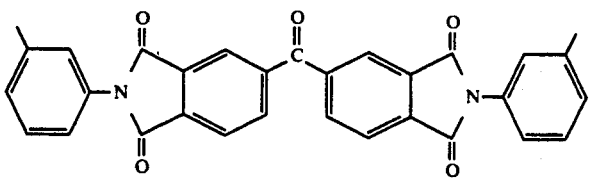

In the most preferred embodiment, $R^1$ is hydrogen, $Ar^1$ is a 4,4'-isopropylidenephenyl linkage and $Ar^2$ is one of the two formulae:

The poly(hydroxy ether imides) of this invention are generally prepared by contacting a bisphenol incorporating one or more imide moieties,

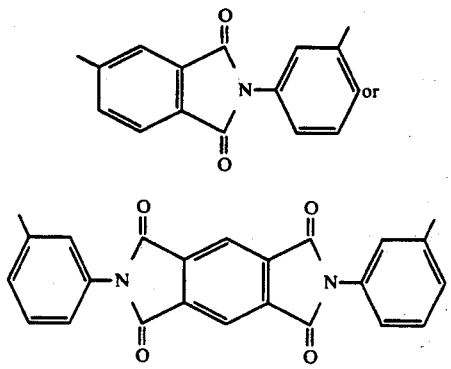

hereinafter referred to as an imide-containing bisphenol, with a diglycidyl ether of the same or another bisphenol under conditions sufficient to cause phenolic hydroxyl moieties to react with epoxy moieties to form a polymer backbone having imide linkages, ether linkages and pendant hydroxyl moieties. Alternatively, the polymers can be formed by reactions of bisphenols not having imide linkages with diglycidyl ethers of imide-containing bisphenols. In both instances, mixtures of bisphenols, imide-containing bisphenols, glycidyl ethers of bisphenols and glycidyl ethers of imide-containing bisphenols can be employed to produce copolymeric poly(hydroxy ether imides). In general, it is desirable for the monomers to react in the presence of a catalyst and a solvent at temperatures ranging from 60° to 200° C.

Preferred catalysts are quaternary ammonium and phosphonium salts, such as tetraethylammonium chloride, tetraethylammonium bromide, tetraethylammonium iodide, tetraethylammonium hydroxide, tetra(n-butyl)ammonium chloride, tetra(n-butyl)ammonium bromide, tetra(nbutyl)ammonium iodide, tetra(n-butyl)ammonium hydroxide, tetra(n-octyl)ammonium chloride, tetra(n-octyl)ammonium bromide, tetra(n-octyl)ammonium iodide, tetra(noctyl)ammonium hydroxide, methyltris(n-octyl)ammonium chloride, ethyltriphenylphosphonium acetate, tetraphenylphosphonium bromide, tetraphenylphosphonium chloride, bis(triphenyl phosphoranylidene)ammonium chloride and tetraphenylphosphonium iodide.

Preferred solvents include dimethylformamide, N-methylpyrrolidone and propylene glycol phenylether. Most preferred conditions are described in the working examples.

Suitable imide-containing bisphenols include but are not limited to N,N'-bis(4-hydroxyphenyl)pyromellitimide, N,N'-bis(3-hydroxyphenyl)pyromellitimide, N,N'-bis(2-hydroxyphenyl)pyromellitimide, N,N'-bis(2,6-dimethyl-4-hydroxyphenyl)pyromellitimide, N,N'-bis(2,6-dibromo-4-hydroxyphenyl)pyromellitimide, N,N'-bis(2,6-dicyano-4-hydroxyphenyl)pyromellitimide, N,N'-bis(4-hydroxyphenyl)benzophenonetetracarboxylic diimide, N,N'-bis(3-hydroxyphenyl)benzophenonetetracarboxylic diimide, N,N'-bis(2-hydroxyphenyl)benzophenonetetracarboxylic diimide, N,N'-bis(2,6-dimethyl-4-hydroxyphenyl)-benzophenonetetracarboxylic diimide, N,N'-(2,6-dibromo-4-hydroxyphenyl)benzophenonetetracarboxylic diimide, N,N'-bis(2,6-dicyano-4-hydroxyphenyl)benzophenonetetracarboxylic diimide, N,N'-bis(2,6-bis{3-[4-(4-hydroxyphenolsulfonyl)phenoxy]phenyl}benzophenonetetracarboxylic diimide, bis{4-4-(4-hydroxyphenylsulfonyl)phenoxy]phenyl}benzophenonetetracarboxylic diimide, N-(4-hydroxyphenyl)-4-hydroxyphthalimide, N-(3-hydroxyphenyl)-4-hydroxyphthalimide, N-(2-hydroxyphenyl)-4-hydrophthalimide, N-(2,6-dimethyl-4-hydroxyphenyl)-4-hydroxyphthalimide, N-(2,6-dibromo-4-hydroxyphenyl)-4-hydroxyphthalimide, N-(2,6-dicyano-4-hydroxyphenyl)-4-hydroxyphthalimide, N-{3-4-(4-hydroxyphenylsulfonyl)-phenoxy]phenyl}-4-hydroxyphthalimide, N-{4-[4-(4-hydroxyphenylsulfonyl)phenoxyphenyl}-4-hydroxyphthalimide, N-(4-hydroxyphenyl)-3-hydroxyphthalimide, N-(3-hydroxyphenyl)-3-hydroxyphthalimide and N-(2-hydroxyphenyl)-3-hydroxyphthalimide. Preferred imide-containing bisphenols are described in the working examples.

Suitable arylene diglycidyl ethers include but are not limited to the diglycidyl ether of 4,4'-isopropylidene bisphenol (bisphenol A), 4,4'-dihydroxydiphenylethylmethane, 3,3'-dihydroxydiphenyldiethylmethane, 3,4'-dihydroxydiphenylmethylpropylmethane, 4,4'-dihydroxydiphenyloxide, 4,4'-dihydroxydiphenylcyanomethane, 4,4'-dihydroxybenzophenone, 4,4'-dihydroxydiphenyl sulfide, 4,4'-dihydroxydiphenyl sulfone, 2,6-dihydroxynapthalene, 9,9-bis(4-hydroxyphenol)-fluorene, phenolphthalein, phenolphthalimidine, N-(2-hydroxyethyl)phenolphthalimidine, N,N'-bis(3-hydroxyphenyl)pyromellitimide, N,N'-bis(4-hydroxyphenyl)-pyromellitimide, N,N'-bis(3-hydroxyphenyl)benzophenonetetracarboxylic diimide, N,N'-bis(4-hydroxyphenyl)benzophenonetetracarboxylic diimide, N-(3-hydroxyphenyl)-4-hydroxyphthalimide, and N-(4-hydroxyphenyl)-4-hydroxyphthalimide. Most preferred is the diglycidyl ether of 4,4'-isopropylidene bisphenol.

The retort-sterilizable articles, for example, containers, films and coatings, of this invention are fabricated from the polymers using conventional fabricating techniques for normally solid thermoplastics such as extrusion, coextrusion, compression molding, casting, blow molding, injection molding and similar fabrication techniques commonly employed to produce such articles.

It is well known that conventional heat resistant, transparent thermoplastics are unsuitable for packaging air-sensitive materials. For example, polycarbonate, with a $T_g$ of 150° C., has a very high oxygen transmission rate (OTR) of 300 cc-mil/100 in²-day-atm. It is also well known that when structural units which decrease the packing density of the polymer chains are present, that the materials generally exhibit higher permeability to gases. For example, the copolyester of terephthalic acid and phenolphthalein has a $T_g$ of 299° C., with a very high oxygen transmission rate of 500 cc-mil/100 in²-day-atm. On the other hand, the polymers of the present invention exhibit a surprising and unusual combination of low permeability to oxygen, transparency and high glass transition temperatures, with OTR values of less than 5 cc-mil/100 in2 day-atm for the polymers shown in Table I.

The following working examples are given to illustrate the invention and should not be construed as limiting its scope. Unless otherwise indicated, all parts and percentages are by weight.

EXAMPLE 1

A. Preparation of N-(4-hydroxyphenyl)-4-hydroxyphthalimide

A mixture of 4-hydroxyphthalic acid (25.05 g, 0.14 mol) and glacial acetic acid (100 mL) is mechanically stirred under a blanket of nitrogen at 110° C. until the material is largely dissolved. Additional acetic acid (30 mL) and p-aminophenol (19.51 g, 0.18 mol) are added, and the mixture is allowed to stir at reflux overnight. The resulting mixture is allowed to cool to room temperature and filtered. Collected solid is washed with acetic acid and dried in vacuo at 120° C. to give yellow powder (27.6 g, 79%, mp 303° C.), which is taken up in boiling acetonitrile (500 mL). The resulting solution is concentrated to 200 mL and allowed to cool to room temperature. Bright yellow crystals (14.0 g) precipitate and are collected and dried as described above. A second crop of product (13.0 g) is obtained by seeding the filtrate, adding ethanol (150 mL) and concentrating to 100 mL. Additional purification is effected by sublimation of the product at 240° C. (<0.01 mm Hg) to give a yellow powder having the following structure:

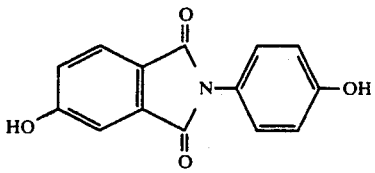

B. Preparation of Poly(hydroxy ether imide) (Polymer 1)

A mechanically stirred mixture of the N-(4-hydroxyphenyl)-4-hydroxyphthalimide (6.285 g, 24.6 mmol) prepared in Part A, methanol-washed DER, 332 (8.883 g, 25.6 mmol) and propylene glycol phenyl ether (8 mL) is heated to 140° C. under a slow nitrogen flow. Ethyltriphenylphosphonium acetate (70% in methanol: 10 drops) is added and the temperature is increased to 150° C. After 10 minutes, the monomers completely dissolve and viscosity of the solution rises as the polymerization proceeds. Thus additional solvent (15 mL total) is added from time-to-time to maintain efficient stirring. After stirring for 2 hours at 160° C., the solution is diluted with DMF (60 mL) and allowed to cool to room temperature. The solution is then added to vigorously stirred (blender) methanol (400 mL) to precipitate a solid that is again blended with methanol and allowed to stir in methanol overnight. The material is dried in vacuo at 90° C., taken up in tetrahydrofuran (100 mL) and again precipitated from methanol. Drying gives Polymer 1 (13.8 g, 91%) as off-white powder with the properties listed in Table I.

EXAMPLE 2

A. Preparation of N-(3-Hydroxyphenyl)-4-hydroxyphthalimide m-Aminophenol(13.23 g, 0.12 mol) and 4-hydroxyphthalic acid (16.98 g, 0.09 mol) are allowed to react in refluxing acetic acid as described above. The product (21.6 g, 91%), collected as a tan solid, is recrystallized from methanol to give 18.5 g of pale yellow powder [mp 270° C. differential scanning calorimetry] having the following structure:

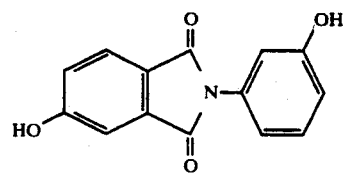

B. Preparation of Poly(hydroxy ether imide) (Polymer 2)

Polymer 2, shown in Table I, is prepared as in Part B of Example 1 except that the imide-containing bisphenol used is N-(3-hydroxyphenyl)-4-hydroxyphthalimide.

EXAMPLE 3

A. Preparation of N,N'-Bis(3-hydroxyphenyl)pyromellitimide

Pyromellitic dianhydride (35.87 g, 0.16 mol) and m-aminophenol (44.87 g, 0.16 mol) are allowed to react as described in Part A of Example 1. The unpurified product [62.0 g, 94%, mp 439° C. (DSC)] is taken up in 1.2 L of DMF at 135° C., and the resulting solution entrated to 800 mL under reduced pressure. Ethanol is added until precipitation occurs at a total volume of 1.5 L (100° C.). The solution is allowed to cool to room temperature overnight and filtered to give a yellow granular solid (49.4 g), which is dried in vacuo at 150° C. The compound has the following structure:

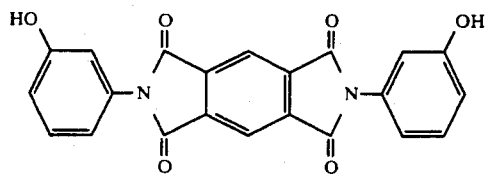

B. Preparation of Poly(hydroxy ether imide) (Polymer 3)

Polymer 3, shown in Table I, is prepared as in Part B of Example 1 except that the imide-containing bisphenol used is N,N'-bis(3-hydroxyphenyl)pyromellitimide.

EXAMPLE 4

A. Preparation of N,N'-Bis(3-hydroxyphenyl)benzophenonetetracarboxylic dimide 3,3',4,4'-Benzophenonetetracarboxylic dianhydride (25.03 g, 0.08 mol) and m-aminophenol (20.77 g, 0.19 mol) are allowed to react in refluxing acetic acid as described above to give the unpurified product as vanilla powder (39.2 g), which is recrystallized from DMF/ethanol to yield N,N'-Bis(3-hydroxyphenyl)benzophenonetetracarboxylic dimide as off-white powder (30.0 g) (mp 365° C.), having the following structure:

B. Preparation of Poly(hydroxy ether imide) (Polymer 4)

Polymer 4, shown in Table I, is prepared as in Part B of Example 1 except that the imide-containing bisphenol used is N,N'-bis(3-hydroxyphenyl)benzophenonetetracarboxylic dimide.

Polymers 1–4 have the general formula:

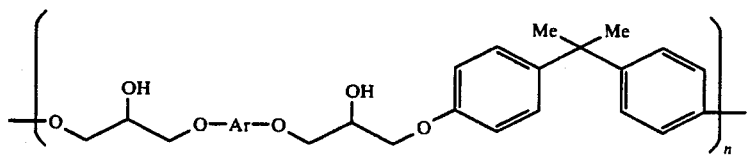

wherein Ar is as shown in Table I.

The data in Table I show that the polymers of the present invention possess good barrier (i.e., oxygen transmission rate less than 10.0 cm$^3$-mil/100 in$^2$-atm-day to oxygen) and high heat resistance (i.e., $T_g$ above 120° C.

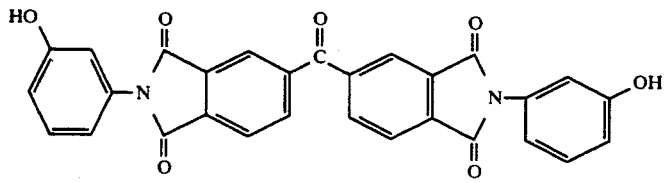

TABLE I

| No. | —Ar— | IV, dL/g$^a$ | Tg, °C.$^b$ | O$_2$TR, DU$^c$ |
|---|---|---|---|---|
| 1 | | 0.68 | 137 | —$^d$ |
| 2 | | 0.50 | 123 | 1.8 |
| 3 | | 0.51 | 151 | 3.3 |

TABLE I-continued

| No. | —Ar— | IV, dL/g[a] | Tg, °C[b] | O₂TR, DU[c] |
|---|---|---|---|---|
| 4 | 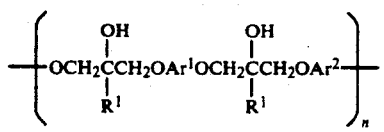 | 0.38 | 152 | —[d] |

[a]DMF, 0.5 g/dL, 25° C.
[b]Determined by differential scanning calorimetry (DSC) using a heating rate of 10° C./min; $T_g$ were measured at the midpoint of the change in slope in the trace of CP vs. temperature.
[c]Cm³-mil/100 in²-atm-day; determined for compression molded films (5–10 mil) at 23° C. under the conditions of ASTM Method D-3985; relative humidity of the oxygen stream was 59–68%.
[d]Not tested.

What is claimed is:

1. A thermoplastic polymer having excellent barrier to oxygen and represented by the formula:

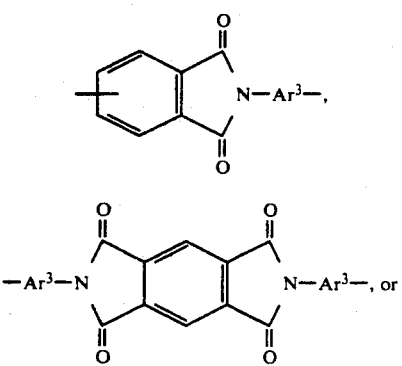

wherein n is an integer from 10 to 1000, $R^1$ is independently a hydrogen or hydrocarbyl moiety, $Ar^1$ is a non-imide-containing arylene linkage, and $Ar^2$ is an imide-containing arylene linkage represented by any one of the formulae:

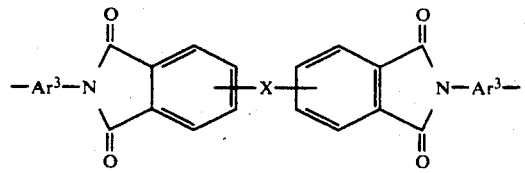

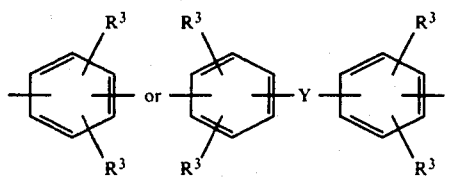

wherein X is a linking group which is a covalent bond, hydrocarbylene, oxygen, sulfur, or sulfonyl, and $Ar^3$ has one of the formulae:

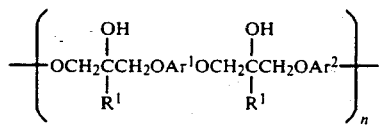

wherein $R^3$ is a hydrogen, unsubstituted hydrocarbyl, substituted hydrocarbyl, wherein the substituent(s) is an inert monovalent moiety, halo or cyano moiety, and Y is a covalent bond, hydrocarbylene, oxygen, sulfur, sulfonyl or carbonyl linkage.

2. The polymer of claim 1 wherein $R^1$ is hydrogen and Aris 4,4'-isopropylidenediphenyl.

3. The polymer of claim 2 wherein $Ar^2$ has the formula:

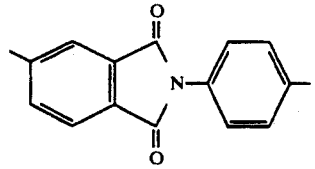

4. The polymer of claim 2 wherein $Ar^2$ has the formula:

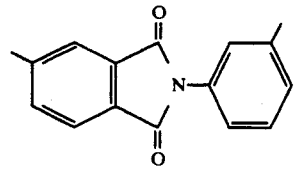

5. The polymer of claim 2 wherein $Ar^2$ has the formula:

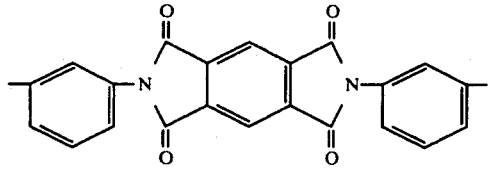

6. The polymer of claim 2 having a $T_g$ of greater than 120° C. and an OTR of less than 10.0 cm³-mil/100 in²-atm-day.

7. A thermoplastic polymer, in the form of a container, having excellent barrier to oxygen and represented by the formula:

$$\left\{ -OCH_2\underset{R^1}{\underset{|}{\overset{OH}{\overset{|}{C}}}}CH_2OAr^1OCH_2\underset{R^1}{\underset{|}{\overset{OH}{\overset{|}{C}}}}CH_2OAr^2- \right\}_n$$

wherein n is an integer from 10 to 1000, $R^1$ is independently a hydrogen or hydrocarbyl moiety, $Ar^1$ is a nonimide-containing arylene linkage, and Ar² is an imide-containing arylene linkage represented by any one of the formulae:

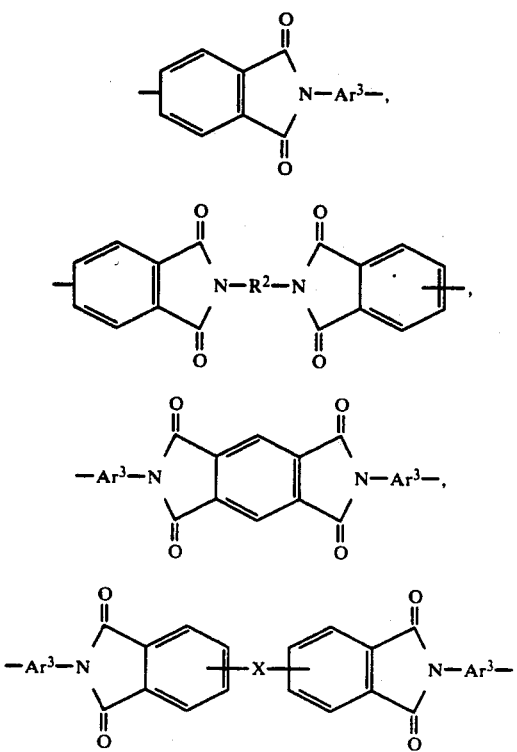

wherein R² is hydrocarbylene which may optionally contain hetero atoms selected from the group consisting of sulfur, oxygen and nitrogen, X is a linking group which is a covalent bond, hydrocarbylene, oxygen, sulfur, or sulfonyl, and Ar³ has one of the formulae:

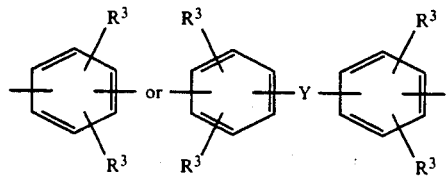

wherein R³ is a hydrogen, unsubstituted hydrocarbyl, substituted hydrocarbyl, wherein the substituent(s) is an inert monovalent moiety, halo or cyano moiety, and Y is a covalent bond, hydrocarbylene, oxygen, sulfur, sulfonyl or carbonyl linkage.

8. A thermoplastic polymer, in the form of a film, having excellent barrier to oxygen and represented by the formula:

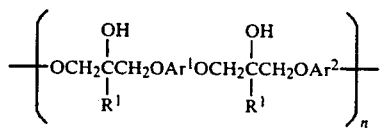

wherein n is an integer from 10 to 1000, R¹ is independently a hydrogen or hydrocarbyl moiety, Ar¹ is a non-imide-containing arylene linkage, and Ar² is an imide-containing arylene linkage represented by any one of the formulae:

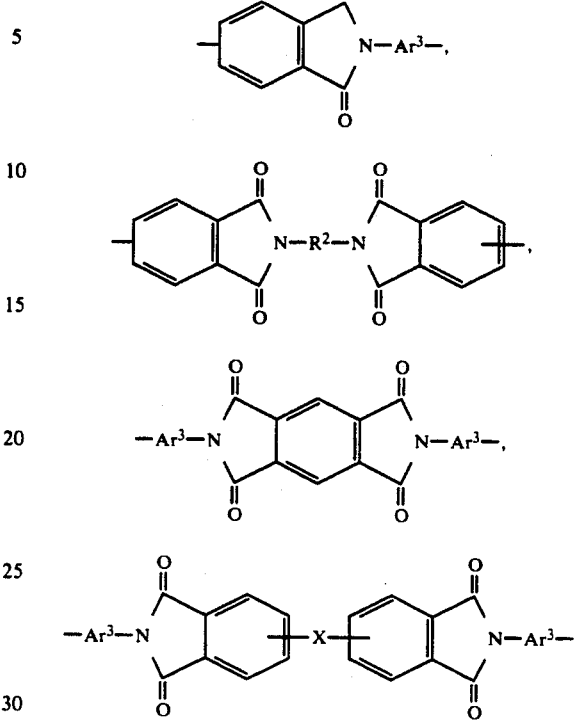

wherein R² is hydrocarbylene which may optionally contain hetero atoms selected from the group consisting of sulfur, oxygen and nitrogen, X is a linking group which is a covalent bond, hydrocarbylene, oxygen, sulfur, or sulfonyl, and Ar³ has one of the formulae:

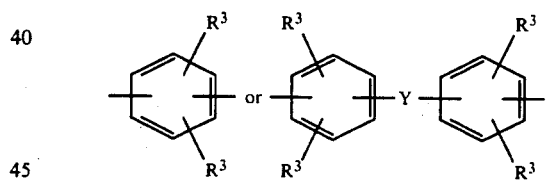

wherein R³ is a hydrogen, unsubstituted hydrocarbyl, substituted hydrocarbyl, wherein the substituent(s) is an inert monovalent moiety, halo or cyano moiety, and Y is a covalent bond, hydrocarbylene, oxygen, sulfur, sulfonyl or carbonyl linkage.

9. A thermoplastic polymer, in the form of a coating, having excellent barrier to oxygen and represented by the formula:

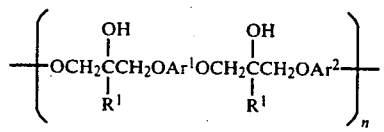

wherein n is an integer from 10 to 1000, R¹ is independently a hydrogen or hydrocarbyl moiety, Ar¹ is a non-imide-containing arylene linkage, and Ar² is an imide-containing arylene linkage represented by any one of the formulae:

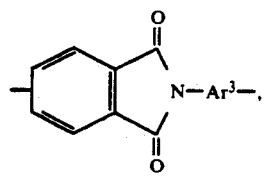

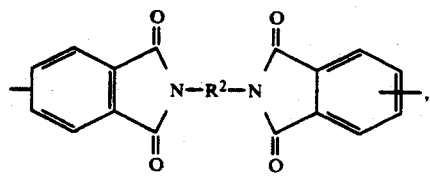

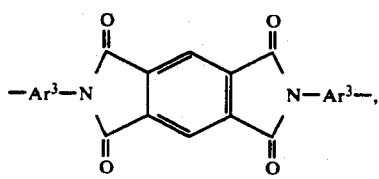

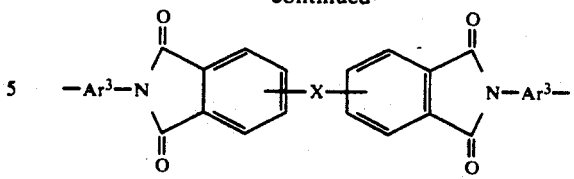

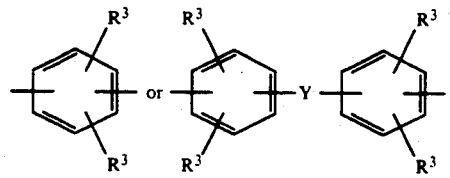

wherein $R^2$ is hydrocarbylene which may optionally contain hetero atoms selected from the group consisting of sulfur, oxygen and nitrogen, X is a linking group which is a covalent bond, hydrocarbylene, oxygen, sulfur, or sulfonyl, and $Ar^3$ has one of the formulae:

wherein $R^3$ is a hydrogen, unsubstituted hydrocarbyl, substituted hydrocarbyl, wherein the substituent(s) is an inert, monovalent moiety, halo or cyano moiety, and Y is a covalent bond, hydrocarbylene, oxygen, sulfur, sulfonyl or carbonyl linkage.

* * * * *

UNITED STATES PATENT AND TRADEMARK OFFICE
CERTIFICATE OF CORRECTION

PATENT NO. : 5,246,751

DATED : September 21, 1993

INVENTOR(S) : Jerry E. White, Edmund J. Stark, Anthony P. Haag, Daniel J. Murray It is certified that error appears in the above-identified patent and that said Letters Patent is hereby corrected as shown below:

Col. 10, line 20, "Aris" should read -- "$Ar^1$ is" --.

Col. 10, line 53, "2" should read -- "1" --.

Signed and Sealed this

Twenty-fourth Day of January, 1995

Attest:

BRUCE LEHMAN

Attesting Officer

Commissioner of Patents and Trademarks